(12) United States Patent
Movshovich

(10) Patent No.: US 12,226,342 B1
(45) Date of Patent: Feb. 18, 2025

(54) CORNEAL CUTTER AND METHOD OF USE

(71) Applicant: Alexander Movshovich, New York, NY (US)

(72) Inventor: Alexander Ilich Movshovich, New York, NY (US)

( * ) Notice: Subject to any disclaimer, the term of this patent is extended or adjusted under 35 U.S.C. 154(b) by 0 days.

(21) Appl. No.: 18/656,995

(22) Filed: May 7, 2024

(51) Int. Cl.
- *A61F 9/007* (2006.01)
- *A61B 17/00* (2006.01)
- *A61B 17/3211* (2006.01)
- *A61F 9/00* (2006.01)

(52) U.S. Cl.
CPC ........ *A61F 9/00736* (2013.01); *A61F 9/0017* (2013.01); *A61B 2017/00738* (2013.01); *A61B 17/3211* (2013.01)

(58) Field of Classification Search
CPC ................ A61F 9/00736; A61F 9/0017; A61F 9/013–0133; A61B 17/3211; A61B 2017/00738
See application file for complete search history.

(56) References Cited

U.S. PATENT DOCUMENTS

| | | | |
|---|---|---|---|
| 5,203,865 A * | 4/1993 | Siepser | A61F 9/0133 30/162 |
| 5,258,002 A * | 11/1993 | Jeffers | A61F 9/0133 30/348 |
| 5,370,652 A * | 12/1994 | Kellan | A61F 9/0133 30/294 |
| 5,607,437 A | 3/1997 | Simon | |
| 5,653,725 A | 8/1997 | Simon | |
| 7,722,669 B2 | 5/2010 | Foulkes | |
| 2002/0055753 A1 | 5/2002 | Silvestrini | |
| 2010/0280535 A1* | 11/2010 | Yamaguchi | A61F 9/0133 606/167 |
| 2014/0107631 A1 | 4/2014 | Ferrari | |
| 2015/0305927 A1* | 10/2015 | Walter | A61F 9/0008 606/186 |

FOREIGN PATENT DOCUMENTS

WO 2018122537 A1 7/2018

OTHER PUBLICATIONS

Alió, Jorge L., et al. "Femtosecond-assisted keratopigmentation for functional and cosmetic restoration in essential iris atrophy." Journal of Cataract & Refractive Surgery 37.10 (2011): 1744-1747.
Alió, Jorge L., et al. "Keratopigmentation to change the apparent color of the human eye: a novel indication for corneal tattooing." Cornea 35.4 (2016): 431-437.
(Continued)

*Primary Examiner* — Brigid K Byrd
(74) *Attorney, Agent, or Firm* — Koffsky Schwalb LLC

(57) ABSTRACT

A surgical knife for adjusting size and shape of an intracorneal channel during a keratopigmentation procedure to better match the geometry of the patient's iris and for delivering color pigments into the intracorneal channel. The surgical knife includes a handle, a shaft section, an arcuate section and a kidney-shaped appendage that is coupled to the proximal end of the arcuate section. The kidney-shaped appendage includes a top surface, a bottom surface, a non-cutting sidewall, a cutting sidewall, and a cutting edge extending along the cutting sidewall.

22 Claims, 8 Drawing Sheets

(56) References Cited

OTHER PUBLICATIONS

D'Oria, Francesco, Sabat K. Abu-Mustafa, and Jorge L. Alio. "Cosmetic change of the apparent color of the eye: a review on surgical alternatives, outcomes and complications." Ophthalmology and Therapy 11.2 (2022): 465-477. Printout from https://link.springer.com.

Hasani, Hamidreza, et al. "Keratopigmentation: a comprehensive review." Eye 34.6 (2020): 1039-1046. Pintout from www.https://nature.com.

* cited by examiner

CORNEAL CUTTER AND METHOD OF USE

FIELD OF THE INVENTION

This invention relates to a field of ophthalmology.

BACKGROUND OF THE INVENTION

Keratopigmentation is a procedure involving the placement of pigments inside the cornea. This procedure has gained popularity as a method for altering the cosmetic appearance of the eye. The procedure typically involves the use of a femtosecond laser to create a doughnut shaped annular channel in the cornea, positioned at the center of the eye's visual axis. However, this annular intracorneal channel does not match the irregular shape of patient's iris and is usually smaller than the iris, resulting in a less-than-optimal partial overlay (masking) of the iris by the injected color pigments that are injected into the channel. To address this issue, it is necessary to adjust the size and shape of the intracorneal channel to better match the geometry of the iris.

Adjusting the size and shape of the initially formed intracorneal channel, to better match the geometry of the patient's iris, requires manual cutting. The cutting process typically involves using a surgical knife with a blade, on one side, to expand the channel. Prior art surgical knives, however, do not facilitate accurate cuts during the knives' forward and rearward movements. Accordingly, what is needed is a surgical knife with a blade that facilitates accurate cutting of the intracorneal channel during the knife's forward movement and during its rearward movement.

Another problem with prior art keratopigmentation procedures is that they result in uneven color appearance between the laser-formed regions of the intracorneal channel and the manually cut regions. The reason being is that the color pigments are typically injected into the intracorneal channel after manual cutting. Because, manually cut regions of the intracorneal channel generally have much more uneven surfaces than the surfaces of laser-formed regions, injecting color pigments into the intracorneal channel after manual cutting results in the manually cut regions of the channel collecting more color pigments per unit of surface area, thus making the manually cut regions appear darker (deeper color) to an outside observer than the laser-formed region(s). Accordingly, an improved keratopigmentation procedure is needed that will result in a more even distribution of color across both laser-formed and manually formed regions of the intracorneal channel.

What is also needed is a specialized technique that results in both a more accurate adjustment (expansion) of the intracorneal channel and a more even color pigment distribution across the expanded channel.

SUMMARY OF THE INVENTION

The present invention introduces a novel device for use in keratopigmentation procedures and an enhanced keratopigmentation procedure. The invention incorporates a targeted surgical knife and a specialized method for adjusting the size and shape of the intracorneal channel, addressing the challenge of accurately matching the channel to the geometry of the patient's iris. By using the surgical knife of the present invention, it becomes possible to effectively and accurately adjust the size and shape of the initially formed circular intracorneal channel. This adjustment aims to align to the geometry of patient's iris more closely, ultimately ensuring that the color pigments injected into the intracorneal channel accurately overlay (mask) the natural color of the iris.

The present invention also introduces a novel keratopigmentation procedure that results in a more even distribution of color across the laser-formed and manually formed regions of the intracorneal channel.

The present invention also provides a method that results in both a more accurate adjustment (expansion) of the intracorneal channel and a more even color pigment distribution across the expanded channel.

By offering a precise and efficient solution, the invention aims to ensure that the injected color pigments overlay (mask) the natural color of the iris with accuracy and consistency, ultimately enhancing the aesthetic outcomes of keratopigmentation.

The invented procedure commences with the formation of a circular channel in the patient's cornea, typically created using a laser, such as a femtosecond laser. Subsequently, the procedure involves making one or more radial incisions in the cornea from the front of the eye to access the initially formed intracorneal channel. Following this, color pigments are injected into the intracorneal channel through one or more of the created radial incisions. Subsequently, a surgical knife having a kidney-shaped appendage is used to adjust the size and shape of the intracorneal channel.

Specifically, the kidney-shaped appendage of the novel surgical knife is inserted into the intracorneal channel through one of the radial incisions. At this stage, at least a portion of the kidney-shaped appendage is manipulated within the intracorneal channel, utilizing a back-and-forth motion. Because the knife's edge, running along a cutting sidewall of the kidney-shaped appendage of the surgical knife, has a kidney shaped profile, it facilitates a more accurate cutting of the channel during the knife's back-and-forth movements. Through this manual cutting process, facilitated by the invented surgical knife (corneal cutter), the boundaries of the channel are expanded to better align with the geometry of the iris.

Finally, either during the manual cutting step using the invented knife or following the manual cutting step, the previously injected color pigments are spread within the enlarged intracorneal channel.

Unlike the existing techniques, the proposed enhanced keratopigmentation procedure offers precise control during the procedure, enabling customizable outcomes tailored to individual preferences and various shapes of the patient's iris. As a result, the invention represents a significant advancement in ophthalmic aesthetics, presenting a safe and effective solution for keratopigmentation with broad applicability and favorable outcomes.

In one embodiment, the invention enables the adjustment of the intracorneal channel's size and shape simultaneously with the spreading of color pigments, streamlining the procedure and optimizing results.

Alternatively, another embodiment allows for the spreading of color pigments to occur following the channel adjustment step, providing flexibility in the sequence of the procedure.

In another embodiment, different color pigments are injected into different sections of the intracorneal channel through previously created two or more radial incisions. This results in the eye appearing to have two or more different colors.

In one embodiment of the present invention, a surgical knife includes a shaft section and an arcuate section coupled to the shaft section. The arcuate section includes a kidney-shaped appendage located at a proximal end of the arcuate section, wherein the kidney-shaped appendage includes a cutting edge stretching along a cutting sidewall of the kidney-shaped appendage.

In one embodiment, the kidney-shaped appendage has a curved front region and a curved rear region, and wherein the cutting edge stretches along the cutting sidewall from the curved front region to the curved rear region.

The cutting edge facilitates enlargement of an intracorneal channel during a forward movement of the kidney-shaped appendage in the intracorneal channel and during a rearward movement of the kidney-shaped appendage in the intracorneal channel. Enlargement of the intracorneal channel during the rearward movement of the kidney-shaped appendage is facilitated by a portion of the cutting edge along the curved rear region of the cutting sidewall.

In one embodiment, the kidney-shaped appendage includes a first surface and a second surface, wherein the cutting sidewall extends between the first surface and the second surface in a beveled fashion, and wherein the cutting edge is located at an interface between the cutting sidewall and the second surface.

In another embodiment, the kidney-shaped appendage includes a first surface and a second surface, wherein the cutting sidewall comprises a first beveled section extending from the first surface and a second beveled section extending from the second surface, and wherein the cutting edge is formed at an interface between the first beveled section and the second beveled section.

In one embodiment, the shaft section includes a handle.

In one embodiment, the invented surgical knife is used to spread color pigments in the intracorneal channel, including the expanded regions of the channel.

In one embodiment, a keratopigmentation system of the present invention includes a laser for forming an intracorneal channel and a novel surgical knife for expanding the channel. In one embodiment, the laser may be a femtosecond laser.

In one embodiment, the invented method for performing an ophthalmological procedure involves using a surgical knife that includes (i) a shaft section and (ii) an arcuate section coupled to the shaft section, the arcuate section including a kidney-shaped appendage located at a proximal end of the arcuate section, the kidney-shaped appendage having a curved front region and a curved rear region, wherein a cutting edge of the kidney-shaped appendage stretches along a cutting sidewall of the kidney-shaped appendage. The method includes the steps of: forming an intracorneal channel; making a radial incision in the cornea, to reach the intracorneal channel; injecting a plurality of color pigments into the intracorneal channel; inserting the kidney-shaped appendage of the surgical knife into the intracorneal channel; and using the cutting edge of the kidney-shaped appendage of the surgical knife to enlarge the intracorneal channel.

In one embodiment, the invented method further includes the step of using the kidney-shaped appendage to spread the plurality of injected color pigments in the enlarged intracorneal channel.

In one embodiment of the invented method, the spreading step includes moving a color pigment of the plurality of color pigments into an expanded portion of the intracorneal channel.

In one embodiment of the invented method, the step of using the cutting edge to enlarge the intracorneal channel includes cutting of the intracorneal channel while moving the kidney-shaped appendage forward and while moving the kidney-shaped appendage rearward.

In one embodiment of the invented method, the step of cutting the intracorneal channel while moving the kidney-shaped appendage rearward is facilitated by a portion of the cutting edge along the curved rear region of the cutting sidewall of the kidney-shaped appendage.

BRIEF DESCRIPTION OF THE DRAWINGS

The accompanying figures, where like reference numerals refer to identical or functionally similar elements throughout the separate views, together with the detailed description below, are incorporated in, form part of the specification, and serve to further illustrate embodiments of concepts that include the claimed invention and explain various principles and advantages of those embodiments.

Skilled artisans will appreciate that elements in the figures, which form a part of this disclosure, are illustrated for simplicity and clarity and have not necessarily been drawn to scale. For example, the dimensions of some of the elements in the figures may be exaggerated relative to other elements to help improve understanding of embodiments of the present invention.

DETAILED DESCRIPTION OF THE INVENTION

The following detailed description discloses several embodiments of the surgical device and method of the present invention.

The invention is directed at a hand-held surgical knife and a procedure in which the knife is used to expand an intracorneal channel, formed in the cornea during a keratopigmentation procedure, and to further spread the color pigments into the expanded regions of the intracorneal channel.

Keratopigmentation is a specialized surgical procedure that involves depositing color pigment inside the cornea, to cover a person's iris's natural color, thus allowing individuals to aesthetically modify and enhance their eyes color when viewed from the front.

One of the problems this invention addresses is the irregular geometry of the iris of the patient's eye, which geometry does not conform to a perfect geometrical shape, such as a circle or annular donut shape. During a keratopigmentation procedure, a femtosecond laser is typically used to form a circular, doughnut shaped, channel inside the cornea (intracorneal channel), positioned at the center of the eye's visual axis. This circular channel, however, does not match the irregular shape of the iris and is typically made smaller than the iris. To match the channel to the shape of the iris, the invented surgical knife is used to adjust the shape and size of the intracorneal channel by further cutting of the channel. Accordingly, a surgical knife of the present invention is used to further cut along peripheral edges of the intracorneal channel. This manual cutting process with said surgical knife expands the boundary(ies) of the channel to better match the geometry of the patient's iris.

Figure 1A:
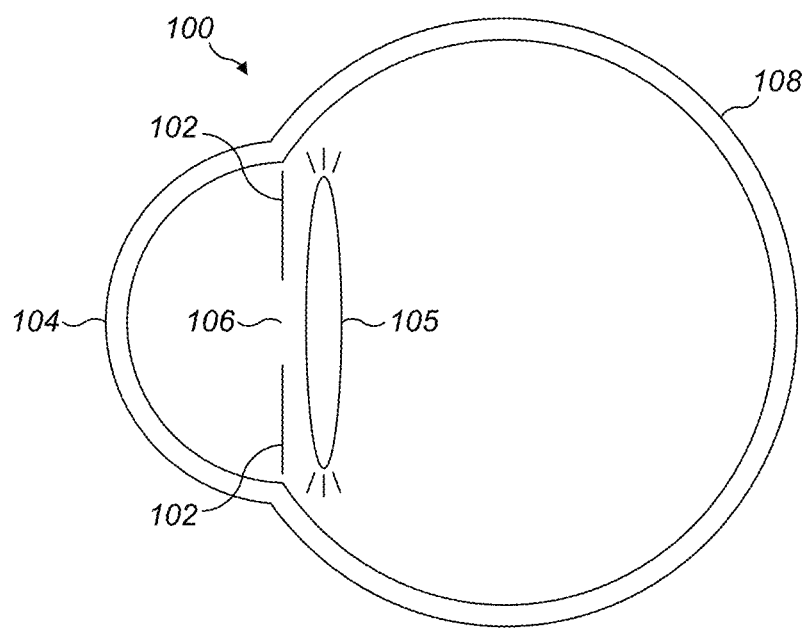
FIGS. 1A and 1B illustrate cross-sectional view and front view, respectively, of human eye.
Figure 1B:
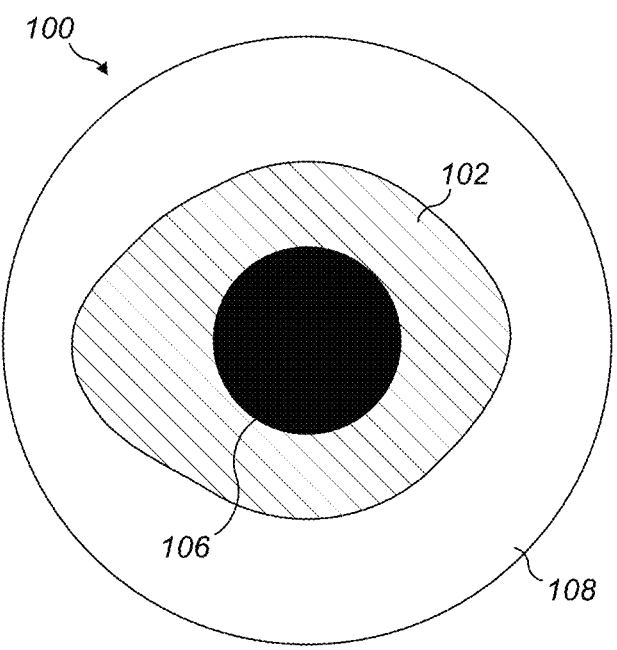

FIGS. 1A and 1B show a cross-sectional view and a frontal view, respectively, of a human eye 100 with an asymmetrical iris prior to undergoing the keratopigmentation procedure, indicating the eye's original color state. (Note that both figures are intended for explanatory purposes only.)

As shown in FIG. 1A, the eye 100 includes a cornea 104, which is a clear layer forming the front portion of the eye that allows light to pass into the eye. Continuous with the cornea 104 is a sclera 108, which is the white outer coating of the eye 100. Sclera is a tough, fibrous tissue that extends from the cornea 104 to the optic nerve at the back of the eye 100.

FIG. 1A also shows an iris 102, which is a thin annular structure located behind the cornea 104 and which determines the eye's natural color. The opening in the center of iris 102 is called pupil 106. Positioned behind the iris 102 is a lens 105, which focuses the incoming light onto the light-sensitive cells of the optic nerve in the back of the eye. These light-sensitive cells are collectively referred to as retina.

To control the amount of light reaching the lens 105, the iris 102 dynamically adjusts the pupil's size. Depending on the changes in ambient lighting conditions, the pupil 106 may dilate (become larger) or contract (become smaller). For example, the pupil 106 may dilate at low lighting levels or contract at high lighting levels.

FIG. 1B depicts the eye 100 of FIG. 1A when viewed from the front. As such, FIG. 1B shows the iris 102 and pupil 106 surrounded by sclera 108. Because the light entering the eye through the pupil does not get reflected back, when viewed from the front, the pupil 106 always appears black.

Figure 2A:
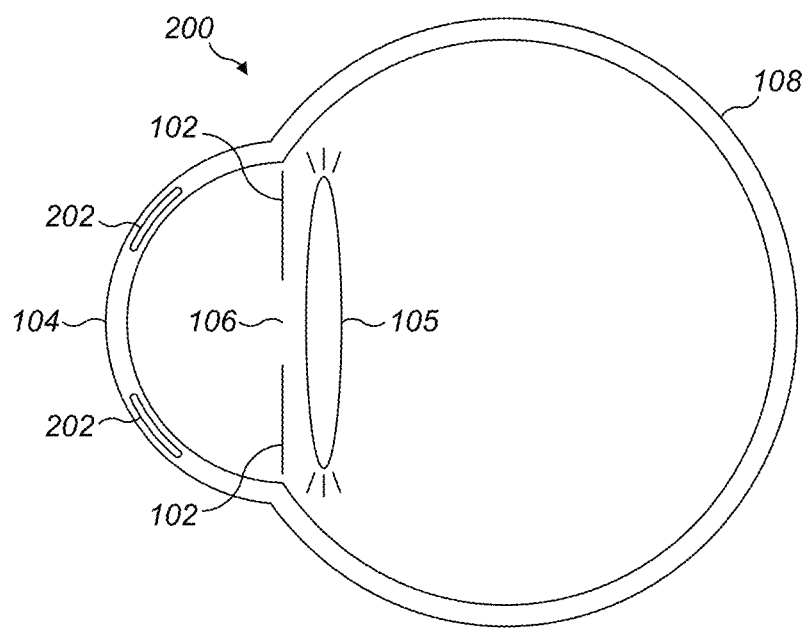
FIGS. 2A and 2B illustrate cross-sectional view and front view, respectively, of human eye during a keratopigmentation procedure according to an embodiment of the invention.
Figure 2B:
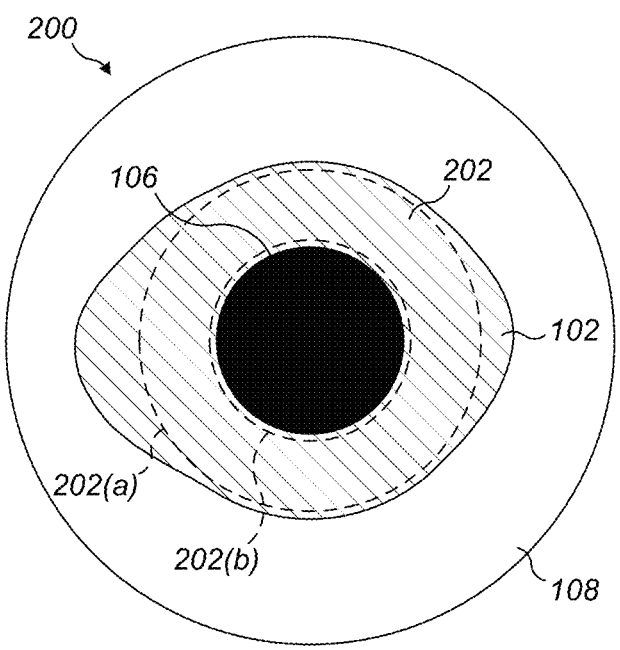

FIGS. 2A and 2B present a cross-sectional view and a front view respectively, of a human eye 200 during a color pigmentation-keratopigmentation-procedure.

The keratopigmentation procedure begins with using a laser, typically a femtosecond laser, to form an annular, doughnut shaped channel inside the cornea 104, i.e., intracorneal channel. This intracorneal channel is designated in FIGS. 2A and 2B by reference numeral 202.

FIG. 2B depicts a circular outer boundary 202 (*a*) and a circular inner boundary 202 (*b*) of the formed channel 202. From FIG. 2B, it is also clear that the laser-formed channel 202 does not overlay the iris 102 completely. For example, to ensure that color pigments, which will be inserted into the channel later in the procedure, will not obstruct the light entering the pupil 106 at any light level, the inner boundary 202 (*b*) of the channel 202 is set to cover the iris 102 up to the point where the pupil is fully dilated. In FIG. 2B, this is conceptually illustrated by having the inner boundary 202 (*b*) positioned outside of the pupil area.

Importantly, as can be seen from FIG. 2B, because of the asymmetric shape of the iris 102, the outer boundary 202 (*a*) of the channel 202 does not follow the geometry of the iris 102. As a result, the iris 102 extends past the outer boundary 202 (*a*) of the channel 202. (For completeness, the figures also show the sclera 108, pupil 106, and lens 105.)

Figure 3:
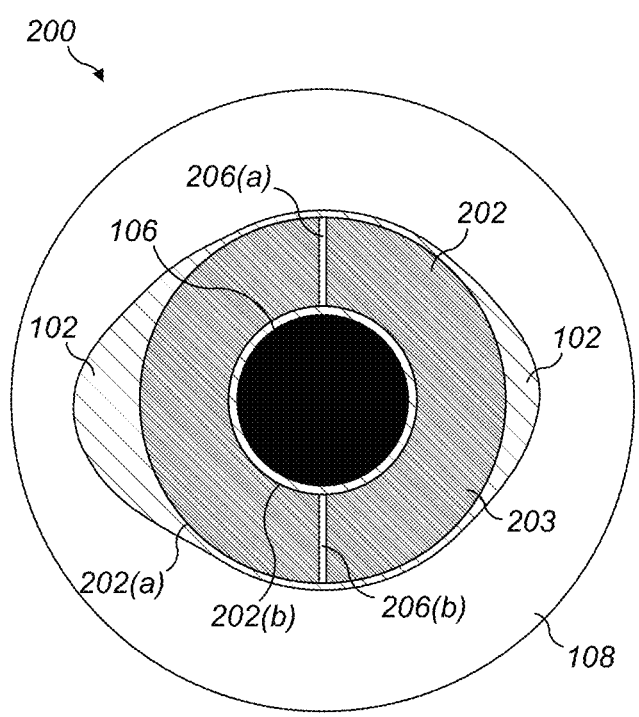
FIG. 3 illustrates a frontal view of a human eye after radial incisions are made in the patient's corneal and color pigments are injected into the intracorneal channel according to an embodiment of the invention.

FIG. 3 illustrates a frontal view of a human eye 200 following the subsequent step of the keratopigmentation procedure. Specifically, the figure depicts the state of procedure after making two radial incisions 206 (*a*) and 206 (*b*) from the front of the eye to access the intracorneal channel 202 and injecting color pigment 203 into the intracorneal channel through one or both radial incisions. As a result, the eye 200 now features radial incisions 206 (*a*) and 206 (*b*) and the intracorneal channel 202 filled with color pigments 203. Because the inner boundary 202 (*b*) of the intracorneal channel was previously set to cover the iris 102 up to a point where the pupil is fully dilated, as depicted in FIG. 3, the color pigments 203 do not obstruct the zone of the pupil 106. Importantly, however, because the iris 102 extends past the outer boundary 202 (*a*) of the channel 202, the injected color pigments 203 do not cover the natural color of the iris 102 in those exterior regions. (Note, in FIG. 3, the sclera 108 is shown for completeness.)

Figure 4A:
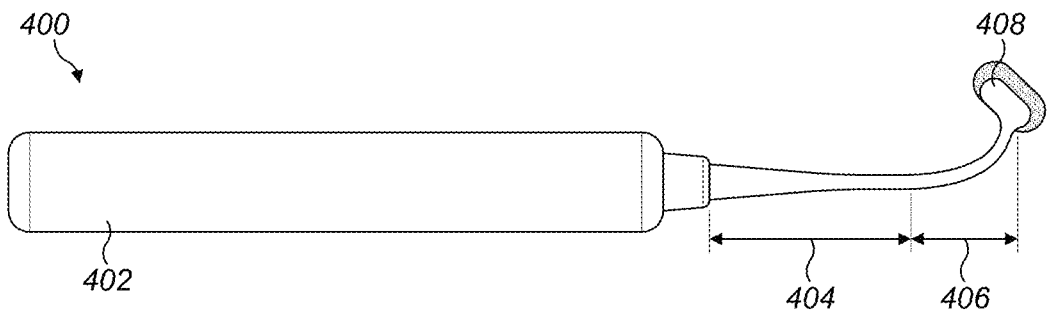
FIGS. 4A, 4B, and 4C depict different views of a surgical knife according to an embodiment of the invention.
Figure 4B:
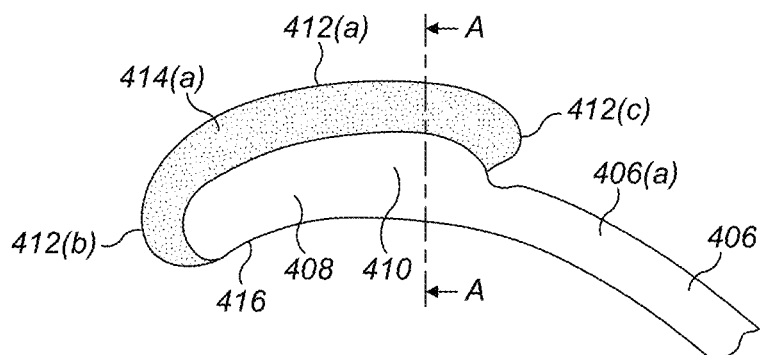
Figure 4C:
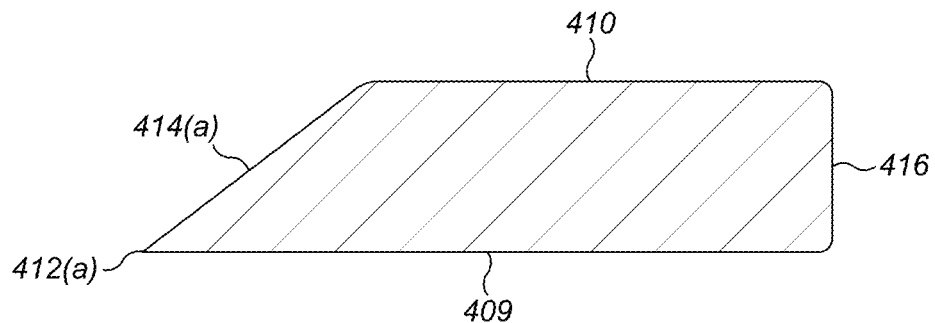

FIGS. 4A, 4B, and 4C depict different views of a surgical knife 400 according to an embodiment of the present invention. The surgical knife 400 in FIG. 4A includes a handle 402, a shaft section 404 and a curved (arcuate) section 406 coupled to the shaft section 404. The arcuate section 406 includes a kidney-shaped appendage 408. In one embodiment, the kidney-shaped appendage 408 may extend in a plane that forms an angle with the longitudinal axis of the handle 402.

FIG. 4B provides a magnified view of the kidney-shaped appendage 408 located at a proximal end 406 (*a*) of the arcuate section 406. The appendage 408 has a first surface (e.g., top surface) 410, a non-cutting sidewall, and a cutting edge 412 (*a*) that extends along a beveled, cutting sidewall 414 (*a*) of the kidney-shaped appendage 408. The appendage 408 further includes a curved front region 412 (*b*) and a curved rear region 412 (*c*), wherein the cutting edge 412 (*a*) stretches along the cutting sidewall 414 (*a*) from the curved front region 412 (*b*) to the curved rear region 412 (*c*).

Due to the unique geometry of the appendage 408 and the extension of its cutting edge 412 (*a*) along the entire length of the cutting sidewall 414 (*a*), the appendage 408 facilitates precise cutting into the walls of the intracorneal channel 202 at the channel's outer 202 (*a*) boundary. This unique geometry of the kidney-shaped appendage 408 allows practitioners to achieve more accurate cuts during forward and rearward movements of the knife in the intracorneal channel 202, thereby enlarging the channel to better match the geometry of the iris 102. For example, the curved rear region 412 (*c*) of the kidney-shaped appendage facilitates cutting of the intracorneal channel during rearward movements of the knife. As a result, except for the pupil area, the color pigments 203 can cover the iris 102 entirely, resulting in improved aesthetic outcomes of the keratopigmentation procedure.

FIG. 4C shows a magnified cross-sectional view taken along line A-A of the kidney-shaped appendage 408 presented in FIG. 4B. FIG. 4C shows the first (e.g., top) surface 410, a second (e.g., bottom) surface 409, a non-cutting sidewall 416, and the cutting sidewall 414 (*a*). A cutting edge 412 (*a*) is formed at an intersection of the cutting sidewall 414 (*a*) and the bottom surface 409. As can be seen from FIG. 4C, the cutting sidewall 414 (*a*) extends between the top and bottom surfaces in a beveled fashion. In the embodiment in FIG. 4C, the sidewall includes a single bevel.

Figure 4D:
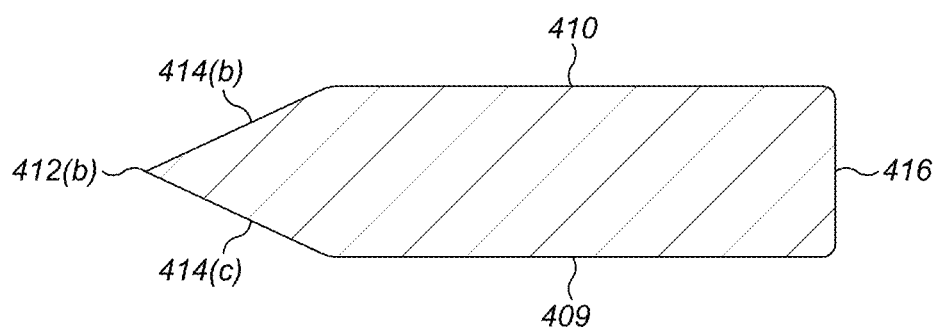
FIG. 4D depicts a cross section of an alternate embodiment of a surgical knife of the present invention.

FIG. 4D shows an alternative embodiment of the invention, in which the cutting sidewall of the kidney-shaped appendage includes two bevels. Specifically, FIG. 4D shows a magnified cross-sectional view taken along line A-A of the alternatively designed kidney-shaped appendage 408 of FIG. 4B. The alternatively designed kidney-shaped appendage 408 has the first (e.g., top) surface 410, the second (e.g., bottom) surface 409, the non-cutting sidewall 416, and a cutting sidewall that includes two beveled sections, 414 (*b*) and 414 (*c*). A cutting edge 412 (*b*) is formed at an interface between the first beveled section 414 (*b*) of the cutting sidewall and the second beveled section 414 (*c*) of the cutting sidewall.

Figure 5:
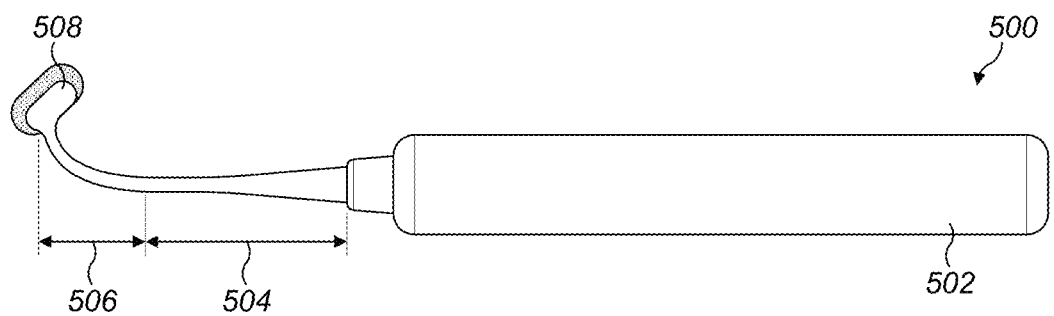
FIG. 5 illustrates a surgical knife which is configured as a mirror image of the surgical knife shown in FIG. 4A.

FIG. 5 presents another embodiment of the hand-held surgical knife of the present invention. In FIG. 5, the surgical knife 500 is designed with a handle 502, a shaft section 504, an arcuate section 506 and a kidney-shaped appendage 508 that are complementary to the arcuate section 406 and kidney-shaped appendage 408 of the surgical knife 400 shown in FIG. 4A. Specifically, the knife 500 depicted in FIG. 5 is configured as a mirror image of the knife 400 shown in FIG. 4A. The descriptions concerning the kidney-shaped appendage 408 in FIGS. 4B through 4D can apply to the kidney-shaped appendage 508 of FIG. 5.

In one embodiment of the method of the present invention, the knife shown in FIG. 4A could be used to enter the intracorneal channel 202 (FIG. 2A) through the radial incision 206 (*a*) from the right to the left, rotated in counterclockwise fashion and moved in the channel back and forth. Alternatively, the knife shown in FIG. 4A could be used to enter the intracorneal channel 202 through the radial incision 206 (*b*) from the left to the right, rotated in counterclockwise fashion and moved in the channel back and forth. Conversely, the knife shown in FIG. 5 could be used to enter the intracorneal channel 202 through the radial incision 206 (*a*) from the left to the right, rotated clockwise and moved in the intracorneal channel 202 back and forth. Alternatively, the knife shown in FIG. 5 could be used to enter the intracorneal channel 202 through the radial incision 206 (*b*) from the right to the left, rotated in clockwise fashion and moved in the intracorneal channel 202 back and forth.

Figure 6:
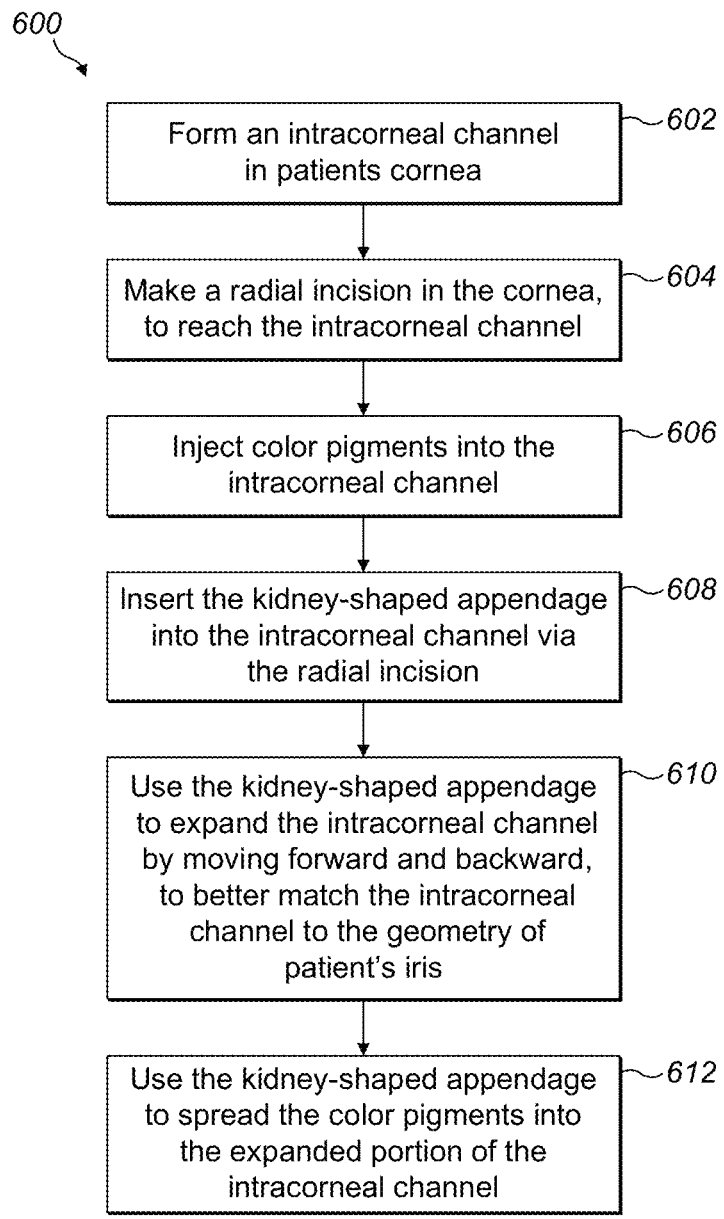
FIG. 6 is a flowchart describing the method according to an embodiment of the present invention.

FIG. 6 illustrates the keratopigmentation procedure (method) 600 according to one embodiment of the present invention.

The method starts at Step 602 by forming an intracorneal channel 202, preferably using the femtosecond laser.

Next, at Step 604, the method continues with the step of making one, or more, radial incisions in the cornea 104 from the front of the eye 200, to reach the intracorneal channel 202. (Note, in an alternative embodiment, where the intracorneal channel is formed manually, the order of steps 602 and 604 is reversed.)

At Step 606, the color pigments are injected into the intracorneal channel 202, via one or more, of the radial incisions. While some of the injected pigments will stick to the upper and lower surface of the intracorneal channel, others may remain floating in the channel.

At Step 608, the kidney-shaped appendage of the surgical knife is manually inserted into the intracorneal channel via one of the radial incisions, with the cutting sidewall of the kidney-shaped appendage facing the outer boundary of the channel.

At Step 610, the kidney-shaped appendage is moved back and forth within the intracorneal channel. This movement within the intracorneal channel cuts the channel further, expanding the outer boundary of the intracorneal channel and enlarging the channel to better match the geometry of the patient's iris.

At Step 612, while cutting to expand the intracorneal channel, the kidney-shaped appendage may be utilized to also spread the previously deposited, floating color pigments into the enlarged regions of the intracorneal channel.

Figure 7:
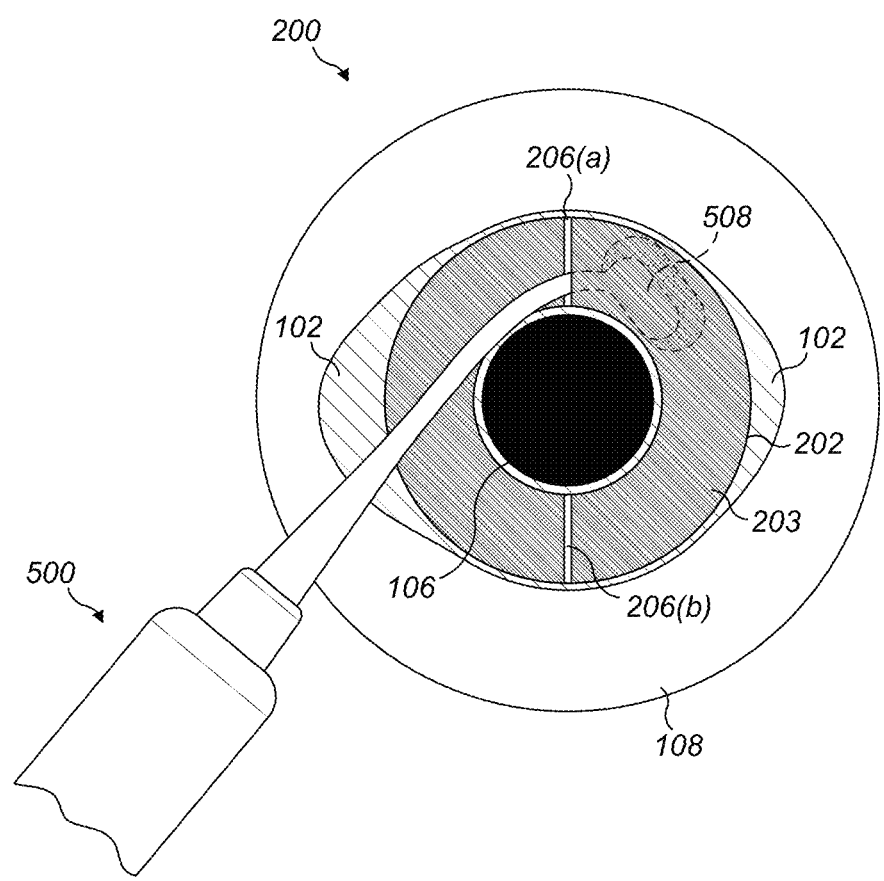
FIG. 7 illustrates a detailed view of the surgical knife shown in FIG. 5 in operation, presenting a front view of a human eye that is undergoing the keratopigmentation procedure according to an embodiment of the present invention.

FIG. 7 shows a more detailed view of the surgical knife 500 in operation, presenting a front view of a human eye 200 that is undergoing the keratopigmentation procedure according to an embodiment of the present invention. In particular, FIG. 7 shows the kidney-shaped appendage 508 of surgical knife 500 inserted into the intracorneal channel 202 through radial incision 206 (*a*). FIG. 7 also shows the sclera 108 and iris 102, including the pupil 106. Finally, FIG. 7 shows the color pigment(s) 203 that was deposited into the intracorneal channel 202 during the previous step of the keratopigmentation procedure.

By inserting the kidney-shaped appendage 508 of the surgical knife 500 into the intracorneal channel 202 via one of the radial incisions and then moving the knife within the intracorneal channel 202 back and forth, one can use the cutting edge of the kidney-shaped appendage to further expand the our boundary the intracorneal channel 202, effectively enlarging or adjusting size and shape of said intracorneal channel to better match the geometry of the iris 102.

Furthermore, either while expanding the intracorneal channel 202 or following the expansion step, one can use the kidney-shaped appendage to spread the previously injected color pigments, that remained floating in the channel, into the manually expanded portion(s) of the channel, thus effectively masking the iris 102. Because the upper and lower surfaces of the manually expanded regions of the channel will be much more uneven than the corresponding surfaces of the laser-formed regions of the channel, spreading of the previously injected pigments into the expanded regions of the channel without further pigment injections results in the mask appearing to have a more even color distribution between the laser-formed and manually-formed regions of the intracorneal channel.

Figure 8A:
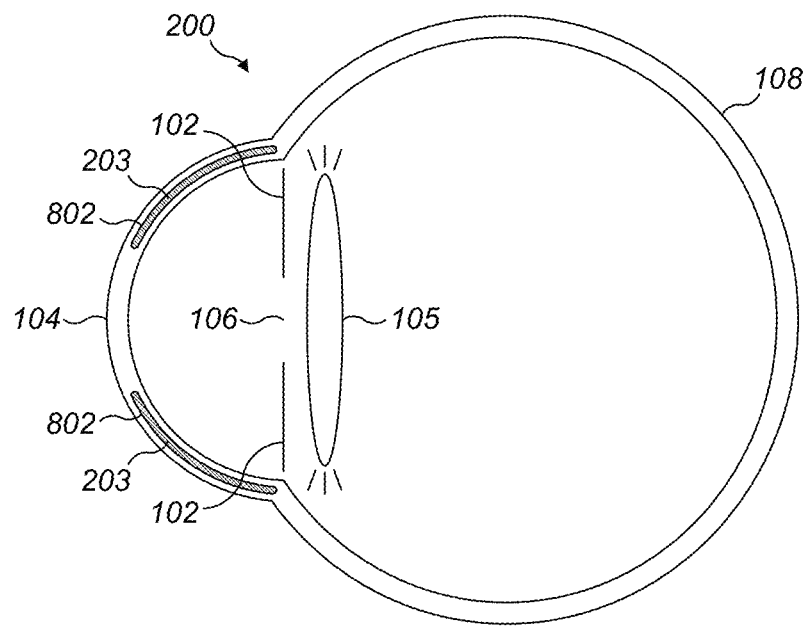
FIGS. 8A and 8B present a cross-sectional view and a front view, respectively, of a human eye after the invented keratopigmentation procedure.
Figure 8B:
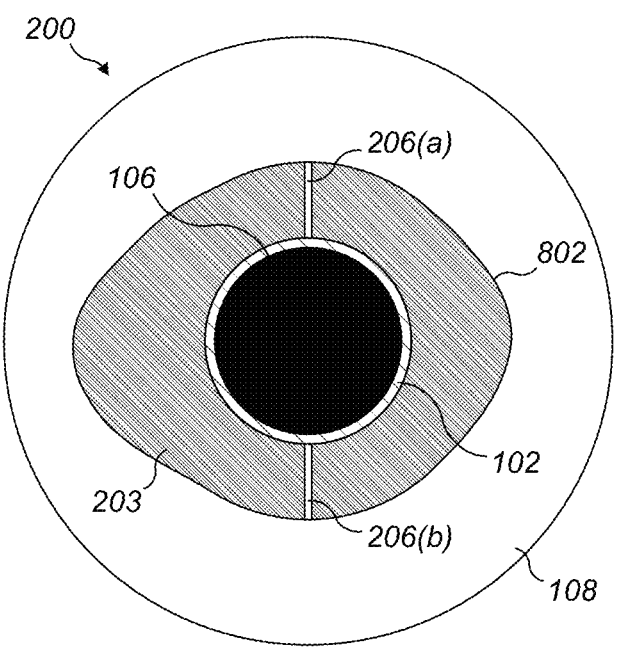

FIGS. 8A and 8B present a cross-sectional view and a front view respectively, of a human eye 200 following the keratopigmentation procedure of the present invention. Specifically, FIG. 8A demonstrates the enlarged intracorneal channel 802 uniformly filled with the color pigments 203.

FIG. 8B shows that the color pigment(s) 203 now accurately masks the natural color of the irregularly shaped iris 102, in contrast with FIG. 3, where the injected color pigments 203 only partially overlay the natural color of said iris 102.

While the foregoing descriptions may disclose specific values, unless expressly stated otherwise, other specific values may be used to achieve similar results. Further, the various features of the foregoing embodiments may be selected and combined to produce numerous variations of improved systems.

In one such variation, the method may include masking the patient's natural eye color with pigments of different colors. For example, pigments of a first color (e.g., brown) may be injected into one region of the intracorneal channel (e.g., masking the left half of the patient's iris) and pigments of a different color (e.g., gold) may be injected into another region of the intracorneal channel (e.g., masking the right half of the patient's iris.) Thus, the invented method contemplates a pigmentation mask that provides not only multicolor pigmentation but also allows for various masking patterns.

In the foregoing specification, exemplary embodiments have been described. However, one of ordinary skills in the art would appreciate that various modifications and changes can be made without departing from the scope of the invention as set forth in the claims below.

The specification and figures are to be regarded in an illustrative rather than a restrictive sense, and all such modifications are intended to be included within the scope of present teachings, and therefore the scope of the invention is to be limited only by the claims.

Moreover, in this document, relational terms such as first and second, up and down, and the like may be used solely to distinguish one entity or action from another entity or action without necessarily requiring or implying any actual relationship or order between such entities or actions. The terms "comprise(s)", "comprising", "has", "having", "includes", "including", "contains", "containing" or any other variation thereof, are intended to cover a non-exclusive inclusion, so that a process, method, article, or apparatus that comprises, has, includes or contains a list of elements does not include only those elements but may include other elements not expressly listed or inherent to such process, method, article, or apparatus. An element preceded by "comprises . . . a", "has . . . a", "includes . . . a" or "contains . . . a" does not, without more constraints, preclude the existence of additional identical elements in the process, method, article, or apparatus that comprises, has, includes, or contains the element. The terms "a" and "an" are defined as one or more unless explicitly stated otherwise herein. The terms "substantially", "essentially", "approximately", "about" or any other version thereof, are defined as being close to as understood by one of ordinary skill in the art. The term "coupled" as used herein is defined as connected, although not necessarily directly. A device or structure that is "configured" in a certain way is configured in at least that way but may also be configured in ways that are not listed.

In addition, in the foregoing Detailed Description, various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

I claim:

1. A surgical knife for expanding a boundary of an annular intracorneal channel, the surgical knife comprising:
    a shaft section; and
    an arcuate section coupled to the shaft section,
    the arcuate section including a kidney-shaped appendage located at a proximal end of the arcuate section,
    wherein the kidney-shaped appendage includes a top surface, a bottom surface, a convex cutting sidewall, and a concave non-cutting sidewall,
    and
    wherein the kidney-shaped appendage includes a cutting edge stretching along the convex cutting sidewall of the kidney-shaped appendage.

2. The surgical knife of claim 1,
    wherein the convex cutting sidewall includes a curved front region and a curved rear region, and
    wherein the cutting edge stretches along the convex cutting sidewall from the curved front region to the curved rear region.

3. The surgical knife of claim 2,
    wherein the cutting edge facilitates enlargement of the annular intracorneal channel during a forward movement of the kidney-shaped appendage in the annular intracorneal channel and during a rearward movement of the kidney-shaped appendage in the annular intracorneal channel.

4. The surgical knife of claim 3, wherein enlargement of the annular intracorneal channel during the rearward movement of the kidney-shaped appendage is facilitated by a portion of the cutting edge along the curved rear region of the convex cutting sidewall.

5. The surgical knife of claim 2, wherein the curved rear region has a bulbous shape.

6. The surgical knife of claim 1,
    wherein the convex cutting sidewall extends between the top surface and the bottom surface, and
    wherein the cutting edge is located at an interface of the convex cutting sidewall and the bottom surface.

7. The surgical knife of claim 1,
    wherein the convex cutting sidewall comprises a first beveled section extending from the top surface and a second beveled section extending from the bottom surface, and
    wherein the cutting edge is formed at an interface between the first beveled section and the second beveled section.

8. The surgical knife of claim 7, wherein the surgical knife facilitates spreading of a color pigment in the annular intracorneal channel.

9. The surgical knife of claim 1, wherein the shaft section comprises a handle.

10. A method of performing an ophthalmological procedure using a surgical knife, the surgical knife including (i) a shaft section and (ii) an arcuate section coupled to the shaft section, the arcuate section including a kidney-shaped appendage located at a proximal end of the arcuate section, the kidney-shaped appendage including a top surface, a bottom surface, a convex cutting sidewall, and a concave non-cutting sidewall, the convex cutting sidewall having a curved front region and a curved rear region, wherein a cutting edge of the kidney-shaped appendage stretches along the convex cutting sidewall,
    the method comprising the steps of:
    making a radial incision in the cornea, to reach an annular intracorneal channel;
    injecting a plurality of color pigments into the annular intracorneal channel;
    inserting the kidney-shaped appendage of the surgical knife into the annular intracorneal channel;
    using the cutting edge of the kidney-shaped appendage of the surgical knife to enlarge the annular intracorneal channel.

11. The method of claim 10, further including a step of using the kidney-shaped appendage to spread the injected plurality of color pigments in the enlarged annular intracorneal channel.

12. The method of claim 11, wherein the step of using the kidney-shaped appendage to spread the injected plurality of color pigments includes moving a color pigment of the injected plurality of color pigments into an expanded portion of the enlarged annular intracorneal channel.

13. The method of claim 10, wherein the step of using the cutting edge to enlarge the annular intracorneal channel includes cutting the annular intracorneal channel while moving the kidney-shaped appendage forward and while moving the kidney-shaped appendage rearward.

14. The method of claim 13,
wherein the step of cutting the annular intracorneal channel while moving the kidney-shaped appendage rearward is facilitated by a portion of the cutting edge along the curved rear region of the convex cutting sidewall of the kidney-shaped appendage.

15. A keratopigmentation system comprising:
a laser for forming an annular intracorneal channel; and
a surgical knife for enlarging the annular intracorneal channel, the surgical knife including:
 a shaft section; and
 an arcuate section coupled to the shaft section,
 wherein the arcuate section includes a kidney-shaped appendage located at a proximal end of the arcuate section,
 wherein the kidney-shaped appendage includes a top surface, a bottom surface, a convex cutting sidewall, and a concave non-cutting sidewall, and
 wherein the kidney-shaped appendage includes a cutting edge stretching along the convex cutting sidewall of the kidney-shaped appendage.

16. The keratopigmentation system of claim 15,
wherein the convex cutting sidewall includes a curved front region and a curved rear region, and
wherein the cutting edge stretches along the convex cutting sidewall from the curved front region to the curved rear region.

17. The keratopigmentation system of claim 16, wherein the cutting edge facilitates enlargement of the annular intracorneal channel during a forward movement of the kidney-shaped appendage in the annular intracorneal channel and during a rearward movement of the kidney-shaped appendage in the annular intracorneal channel.

18. The keratopigmentation system of claim 17, wherein enlargement of the annular intracorneal channel during the rearward movement of the kidney-shaped appendage is facilitated by a portion of the cutting edge along the curved rear region of the convex cutting sidewall.

19. The keratopigmentation system of claim 16, wherein the curved rear region has a bulbous shape.

20. The keratopigmentation system of claim 15,
wherein the cutting sidewall extends between the top surface and the bottom surface, and
wherein the cutting edge is located at an interface between the convex cutting sidewall and the bottom surface.

21. The keratopigmentation system of claim 15,
wherein the convex cutting sidewall comprises a first beveled section extending from the top surface and a second beveled section extending from the bottom surface, and
wherein the cutting edge is formed at an interface between the first beveled section and the second beveled section.

22. The keratopigmentation system of claim 15, wherein the surgical knife includes a handle.

\* \* \* \* \*